US012773377B2

(12) United States Patent
Kurihara

(10) Patent No.: US 12,773,377 B2
(45) Date of Patent: Oct. 27, 2026

(54) WATER-IN-OIL EMULSIFIED SUNSCREEN COSMETIC

(71) Applicant: KAO CORPORATION, Tokyo (JP)

(72) Inventor: Jun Kurihara, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 909 days.

(21) Appl. No.: 17/788,694

(22) PCT Filed: Dec. 24, 2020

(86) PCT No.: PCT/JP2020/048379

§ 371 (c)(1),
(2) Date: Jun. 23, 2022

(87) PCT Pub. No.: WO2021/132444

PCT Pub. Date: Jul. 1, 2021

(65) Prior Publication Data

US 2023/0048396 A1 Feb. 16, 2023

(30) Foreign Application Priority Data

Dec. 25, 2019 (JP) ................................ 2019-234026

(51) Int. Cl.

| | |
|---|---|
| ***A61K 8/06*** | (2006.01) |
| ***A61K 8/27*** | (2006.01) |
| ***A61K 8/29*** | (2006.01) |
| ***A61K 8/36*** | (2006.01) |
| ***A61K 8/58*** | (2006.01) |
| ***A61K 8/92*** | (2006.01) |
| ***A61Q 17/04*** | (2006.01) |

(52) U.S. Cl.

CPC ................ *A61K 8/064* (2013.01); *A61K 8/27* (2013.01); *A61K 8/29* (2013.01); *A61K 8/361* (2013.01); *A61K 8/585* (2013.01); *A61K 8/92* (2013.01); *A61Q 17/04* (2013.01)

(58) Field of Classification Search

None

See application file for complete search history.

(56) References Cited

U.S. PATENT DOCUMENTS

| | | | |
|---|---|---|---|
| 10,383,811 | B1 | 8/2019 | Patel et al. |
| 2021/0052474 | A1 | 2/2021 | Fujinohara |

FOREIGN PATENT DOCUMENTS

| | | | | |
|---|---|---|---|---|
| CN | 101227888 | A | 7/2008 | |
| CN | 103945824 | A | 7/2014 | |
| CN | 104994834 | A | 10/2015 | |
| DE | 10 2005 062 097 | A1 | 7/2007 | |
| EP | 3646850 | A1 * | 5/2020 | ............... A61K 8/34 |
| GB | 2472021 | A | 1/2011 | |
| JP | 2000-204276 | A | 7/2000 | |
| JP | 2003-063931 | A | 3/2003 | |
| JP | 2003-212745 | A | 7/2003 | |
| JP | 2003-335649 | A | 11/2003 | |
| JP | 2015-205832 | A | 11/2015 | |
| JP | 2017-132741 | A | 8/2017 | |
| JP | 2017-178848 | A | 10/2017 | |
| JP | 6567755 | B1 | 8/2019 | |
| JP | 2020-097576 | A | 6/2020 | |
| JP | 2021-031425 | A | 3/2021 | |
| WO | WO 2018/062469 | A1 | 4/2018 | |

OTHER PUBLICATIONS

Extended European Search Report issued on Jan. 2, 2024 for European Patent Application No. 20905207.5, 8 pages.

International Search Report issued Mar. 23, 2021 in PCT/JP2020/048379 filed on Dec. 24, 2020, 3 pages.

Yan Shixiang, "Cosmetic Science vol. 2", Scientific and Technical Documentation Press, Oct. 1998, pp. 152, (with English Summary (Concise explanation)).

* cited by examiner

*Primary Examiner* — Nannette Holloman

(74) *Attorney, Agent, or Firm* — Oblon, McClelland, Maier & Neustadt, L.L.P.

(57) ABSTRACT

Provided is a water-in-oil emulsified sunscreen cosmetic having easiness to spread while applying and is unlikely to decrease SPF value when the applied site is wet with water while containing a high content of the hydrophobized ultraviolet scattering agent.

A water-in-oil emulsified sunscreen cosmetic containing the following components (A), (B), (C), and (D):

(A) 10 mass % or more and 50 mass % or less of a hydrophobized ultraviolet scattering agent, (B) a dipolyhydroxystearic acid ester of a polyhydric alcohol, (C) 35 mass % or more and 85 mass % or less of a liquid oil agent, and (D) water;

wherein a mass ratio of the component (B) to the component (A), [(B)/(A)], is 0.01 or more and 0.2 or less.

20 Claims, No Drawings

WATER-IN-OIL EMULSIFIED SUNSCREEN COSMETIC

CROSS-REFERENCE TO RELATED APPLICATIONS

The present application is a 35 U.S.C. § 371 national stage application of International patent application PCT/JP2020/048379, filed Dec. 24, 2020, which is based on and claims the benefit of priority to Japanese Application No. 2019-234026, filed Dec. 25, 2019. The entire contents of these applications are incorporated herein by reference.

FIELD OF THE INVENTION

The present invention relates to a water-in-oil emulsified sunscreen cosmetic.

BACKGROUND OF THE INVENTION

Sunscreen cosmetics generally contain ultraviolet absorbing agents and ultraviolet scattering agents in order to obtain ultraviolet protection performance (Patent Literatures 1 and 2); however, recently, since cosmetics that are gentler on the skin are demanded, non-chemical sunscreen cosmetics not containing organic ultraviolet absorbing agents are paid attention to.

In non-chemical sunscreen cosmetics, in order to obtain high ultraviolet protection performance without containing ultraviolet absorbing agents, it is necessary to increase the contents of the ultraviolet scattering agents in the sunscreen cosmetics. As such a cosmetic, for example, a water-in-oil emulsified composition containing an organically modified clay mineral, glyceryl (behenate/eicosadioate), polyethylene glycol (30) dipolyhydroxystearate, and the like together with a large content of a fine particle pigment is known (Patent Literature 3).

CITATION LIST

Patent Literatures

[Patent Literature 1]: JP-A-2015-205832
[Patent Literature 2]: JP-A-2017-132741
[Patent Literature 3]: JP-A-2017-178848

SUMMARY OF THE INVENTION

The present invention provides a water-in-oil emulsified sunscreen cosmetic comprising the following components (A), (B), (C), and (D):

(A) 10 mass % or more and 50 mass % or less of a hydrophobized ultraviolet scattering agent, (B) a dipolyhydroxystearic acid ester of a polyhydric alcohol, (C) 35 mass % or more and 85 mass % or less of a liquid oil agent, and (D) water;

wherein a mass ratio of the component (B) to the component (A), [(B)/(A)], is 0.01 or more and 0.2 or less.

DETAILED DESCRIPTION OF THE INVENTION

The water-in-oil emulsified composition described in Patent Literature 3 has insufficiency in spreading while applying due to the increased content of the fine particle pigment.

The present inventor examined the performance of water-in-oil emulsified cosmetics having increased contents of hydrophobized ultraviolet scattering agents, to find that in spite of the fact that water-in-oil emulsified cosmetics are considered to generally have high water resistance, water-in-oil emulsified cosmetics having increased contents of hydrophobized ultraviolet scattering agents are likely to decrease the SPF value when the cosmetic applied site is wet with water.

The present invention relates to provision of a water-in-oil emulsified sunscreen cosmetic that is easy to spread while applying and is unlikely to decrease the SPF value when the applied site is wet with water although containing a high content of a hydrophobized ultraviolet scattering agent.

The present inventor found that a water-in-oil emulsified sunscreen cosmetic including, in addition to a high content of a hydrophobized ultraviolet scattering agent and water, a dipolyhydroxystearic acid ester of a polyhydric alcohol in a specific mass ratio to the hydrophobized ultraviolet scattering agent together with a specific amount of a liquid oil agent is easy to spread while applying and is unlikely to decrease the SPF value when the applied site is wet with water although containing a high content of the hydrophobized ultraviolet scattering agent, to accomplish the present invention.

The water-in-oil emulsified sunscreen cosmetic of the present invention is easy to spread while applying and is unlikely to decrease the SPF value when the applied site is wet with water although containing a high content of the hydrophobized ultraviolet scattering agent. In addition, in spite of a high content of the hydrophobized ultraviolet scattering agent, white residue after application is also unlikely to occur.

<Component (A)>

The water-in-oil emulsified sunscreen cosmetic of the present invention contains (A) a hydrophobized ultraviolet scattering agent. The hydrophobized ultraviolet scattering agent is preferably a hydrophobized fine particle metal oxide.

As the fine particle metal oxide used in the hydrophobized fine particle metal oxide, one or more fine particle metal oxides selected from the group consisting of zinc oxide, titanium oxide, cerium oxide, iron oxide, and chromium oxide are preferable from the viewpoint of the ease of acquisition. Among these fine particle metal oxides, from the viewpoint of ultraviolet protection performance and so on, one or more fine particle metal oxides selected from the group consisting of zinc oxide, titanium oxide, and cerium oxide are preferable, and one or more fine particle metal oxides selected from the group consisting of zinc oxide and titanium oxide are more preferable. These fine particle metal oxides can contain trace elements having +2 valent or higher. Metals such as iron, zirconium, calcium, manganese, magnesium, and yttrium may be contained in these fine particle metal oxides, alone or in combination of two or more thereof.

In addition, from the viewpoint of ultraviolet protection performance and the like, as the hydrophobized fine particle metal oxide, it is preferable to use at least hydrophobized fine particle titanium oxide, more preferable to use hydrophobized fine particle titanium oxide only or a combination of hydrophobized fine particle titanium oxide and hydrophobized fine particle zinc oxide, and particularly preferable to use a combination of hydrophobized fine particle titanium oxide and hydrophobized fine particle zinc oxide.

The shape of the above "fine particle metal oxide" is not particularly limited, and examples thereof include spherical, plate, rod, spindle, needle, and indefinite shapes.

In addition, the average particle diameter of the above "fine particle metal oxide" is preferably 0.01 μm or more, more preferably 0.012 μm or more, and further more preferably 0.015 μm or more and is preferably 1 μm or less, more preferably 0.8 μm or less, and further more preferably 0.5 μm or less. The specific range of the average particle diameter is preferably 0.01 μm or more and 1 μm or less, more preferably 0.012 μm or more and 0.8 μm or less, and particularly preferably 0.015 μm or more and 0.5 μm or less. The ultraviolet protection performance and the dispersion stability can be enhanced by adjusting the average particle diameter in such a range.

The average particle diameter of a fine particle metal oxide means an average particle diameter measured by a laser diffraction/scattering method.

Examples of the fine particle zinc oxide include FINEX-25, FINEX-30, FINEX-50, and FINEX-75 (manufactured Sakai Chemical Industry Co., Ltd.), MZ300 series, MZ500 series, and MZ700 series (manufactured by Tayca Corporation), and ZnO-350 (manufactured by Sumitomo Osaka Cement Co., Ltd.), which are commercially available. Examples of the fine particle titanium oxide include TTO-55 series and TTO-51 series (manufactured by Ishihara Sangyo Kaisha, Ltd.) and JR series and JA series (manufactured by Tayca Corporation), which are commercially available. Examples of the fine particle cerium oxide include high-purity cerium available from Nikki Co., Ltd. or AGC Seimi Chemical Co., Ltd..

The hydrophobization treatment to the above fine particle metal oxide may be performed using a known surface treatment agent for hydrophobization, and examples thereof include fluorine compound treatment, silicone treatment, silicone resin treatment, pendant treatment, silane coupling agent treatment, titanium coupling agent treatment, oil agent treatment, N-acylated lysine treatment, polyacrylic acid treatment, metal soap treatment, amino acid treatment, inorganic compound treatment, plasma treatment, mechanochemical treatment, silane compound treatment, and silazane compound treatment.

Among these treatments, from the viewpoint of dispersion stability, treatment with silicone or a silicone resin, treatment with a silane compound or a silazane compound, and treatment with metal soap, such as aluminum stearate, aluminum isostearate, or aluminum laurate, are preferable.

Examples of the silicone or silicone resin include methylpolysiloxane, methylphenylpolysiloxane, methylhydrogenpolysiloxane, a methylhydrogenpolysiloxane-dimethylpolysiloxane copolymer, octamethylcyclotetrasiloxane, decamethylcyclopentasiloxane, dodecamethylcyclohexasiloxane, octamethyltrisiloxane, tetradecamethylhexasiloxane, a dimethylsiloxane-methyl(polyoxyethylene)siloxane-methyl(polyoxypropylene)siloxane copolymer, a dimethylsiloxane-methyl(polyoxyethylene)siloxane copolymer, a dimethylsiloxane-methyl(polyoxypropylene)siloxane copolymer, a dimethylsiloxane-methylcetyloxysiloxane copolymer, and a dimethylsiloxane-methylstearoxysiloxane copolymer. As the methylhydrogenpolysiloxane-dimethylpolysiloxane copolymer, those of the following formula (1) are preferable.

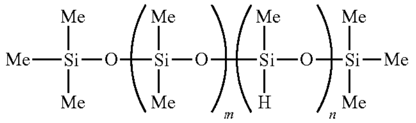

(1)

[In the formula (1), m and n are each an integer of 0 or more, and $1 \leq m+n \leq 60$.]

As the silane compound or the silazane compound above, a silane compound or silazane compound including an alkyl group having from 1 to 20 carbon atoms or a fluoroalkyl group having from 1 to 20 carbon atoms and having reactivity with an inorganic oxide is preferable, and a silane compound of the following formula (2) or a silazane compound of the following formula (3) is more preferable. These compounds may be used alone or in combination of two or more thereof.

$$R^4(R^5)_pSi(Z)_{3-p} \quad (2)$$

[In the formula (2), $R^4$ represents a linear or branched alkyl group having from 1 to 20 carbon atoms or a linear or branched fluoroalkyl group having from 1 to 20 carbon atoms, $R^5$ represents a linear or branched alkyl group having from 1 to 6 carbon atoms, Z represents a halogen atom or an alkoxy group, and p represents 0 or 1.]

$$R^6R^7R^8SiNHSiR^9R^{10}R^{11} \quad (3)$$

[In the formula (3), $R^6$ to $R^{11}$ each independently represent a linear or branched alkyl group having from 1 to 20 carbon atoms or a linear or branched fluoroalkyl group having from 1 to 20 carbon atoms.]

As the silane compound, from the viewpoint of dispersion stability, and the like, alkylalkoxysilane or fluoroalkylalkoxysilane is preferable, and alkyltrialkoxysilane or fluoroalkyltrialkoxysilane is more preferable. Specifically, examples thereof include hexyltrimethoxysilane, octyltrimethoxysilane, octyltriethoxysilane, decyltrimethoxysilane, octadecyltrimethoxysilane, trifluoropropyltrimethoxysilane, and heptadecafluorodecyltrimethoxysilane. These compounds may be used alone or in combination of two or more thereof. Among these compounds, octyltrimethoxysilane and octyltriethoxysilane are particularly preferable.

In addition, as the silazane compound, for example, hexamethyldisilazane is specifically mentioned.

The coating amount of the surface treatment agent used in the hydrophobization treatment is preferably 3 parts by mass or more, more preferably 5 parts by mass or more, based on 100 parts by mass of the fine particle metal oxide from the viewpoint of emulsion stability, dispersion stability, and the like and is preferably 15 parts by mass or less, more preferably 10 parts by mass or less, based on 100 parts by mass of the fine particle metal oxide from the viewpoint of emulsion stability, dispersion stability, and the like.

The hydrophobization treatment can be performed by a conventionally known method appropriately selected. For example, as treatment with silicone or a silicone resin described above, as described in JP-B-3187440, mentioned is a method for coating the surface of a fine particle metal oxide with silicon oxide by coating the fine particle metal oxide in non-gas phase using at least one or more of organopolysiloxanes and silicone compounds consisting of silicone resins (provided that silane compounds are excluded) and then performing burning in an oxygen-containing atmosphere at a temperature of from 600° C. to 950° C.

Examples of the treatment method using a silane compound or a silazane compound include a chemical bonding method. More specifically, for example, mentioned is a method of mixing a silane compound or a silazane compound and a fine particle metal oxide in an organic solvent, such as n-hexane, cyclohexane, or lower alcohol, performing pulverization as needed, and then removing the organic solvent by heating (for example, at from 80° C. to 250° C.) or reduced pressure. In addition, mentioned is a method of performing coating treatment with a polysiloxane compound and then performing surface treatment with a silane compound in water as described in JP-A-2007-326902.

The hydrophobized ultraviolet scattering agents may be used alone or in combination of two or more thereof.

The content of the hydrophobized ultraviolet scattering agent in the water-in-oil emulsified sunscreen cosmetic of the present invention is 10 mass % or more and 50 mass % or less. When the content of the hydrophobized ultraviolet scattering agent is 10 mass % or more, high ultraviolet protection performance can be obtained even when the content of the ultraviolet absorbing agent is reduced or even when the ultraviolet absorbing agent is not used.

The content of the hydrophobized ultraviolet scattering agent in the water-in-oil emulsified sunscreen cosmetic of the present invention is preferably 12.5 mass % or more, more preferably 15 mass % or more, further more preferably 20 mass % or more, and particularly preferably 22.5 mass % or more from the viewpoint of ultraviolet protection performance, sebum suppressive effect, and the like, and is 50 mass % or less, preferably 40 mass % or less, more preferably 35 mass % or less, and further more preferably 32.5 mass % or less from the viewpoint of absence of white residue, non-powderiness, and the like. The specific range in the water-in-oil emulsified sunscreen cosmetic of the present invention is preferably 12.5 mass % or more and 50 mass % or less, more preferably 15 mass % or more and 40 mass % or less, further more preferably 20 mass % or more and 35 mass % or less, and particularly preferably 22.5 mass % or more and 32.5 mass % or less. The water-in-oil emulsified sunscreen cosmetic of the present invention is easy to spread while applying, is unlikely to cause white residue after application, and is unlikely to decrease the SPF value when the applied site is wet with water, even when the content of the hydrophobized ultraviolet scattering agent is in such a range.

<Component (B)>

The dipolyhydroxystearic acid ester of a polyhydric alcohol is a compound in which polyhydroxystearic acid is ester-bonded to each of two hydroxy groups of the polyhydric alcohol. The polyhydroxystearic acid preferably has an average molecular weight of from 1,000 to 3,000.

Examples of the polyhydric alcohol above include glycols and glycerols. Examples of the glycols include alkylene glycol, such as ethylene glycol, propylene glycol, and 1,3-butylene glycol; dialkylene glycol, such as diethylene glycol and dipropylene glycol; and polyalkylene glycol, such as polyethylene glycol and polypropylene glycol. Examples of the glycerols include glycerol, diglycerol, and polyglycerol.

Among these polyhydric alcohols, from the viewpoint of difficulty in reduction of the SPF value when the applied site is wet with water (hereinafter, in the present specification, the difficulty in reduction of the SPF value when the applied site is wet with water is also expressed as "water resistance"), ease of acquisition, ease of mixing, and the like, dialkylene glycol, polyalkylene glycol, diglycerol, and polyglycerol are preferable, polyalkylene glycol is more preferable, and polyethylene glycol is particularly preferable.

As the dipolyhydroxystearic acid ester of a polyhydric alcohol, from the viewpoint of water resistance, ease of acquisition, emulsion stability, and the like, polyalkylene glycol dipolyhydroxystearate and polyglyceryl-2 dipolyhydroxystearate are preferable, polyalkylene glycol dipolyhydroxystearate is more preferable, polyethylene glycol dipolyhydroxystearate is further more preferable, and polyethylene glycol (30) dipolyhydroxystearate is particularly preferable.

The polyalkylene glycol dipolyhydroxystearate preferably has an average addition number of mols of alkylene oxide of from 5 to 150, more preferably from 10 to 50.

The dipolyhydroxystearic acid ester of a polyhydric alcohol may be a commercially available one or may be synthesized in accordance with a conventional method. Examples of the method for synthesizing the dipolyhydroxystearic acid ester of a polyhydric alcohol include a method in which a polyhydric alcohol is reacted, in the presence of an alkali, with an acid halide prepared by a reaction of a halogenating agent, such as thionyl chloride, with polyhydroxystearic acid.

Examples of the commercial product of polyethylene glycol (30) dipolyhydroxystearate include Cithrol DPHS (manufactured by Croda Japan K.K.) and Arlacel P135 (manufactured by Uniqema). Examples of the commercial product of polyglyceryl-2 dipolyhydroxystearate include DEHYMULS PGPH (manufactured by Henkel AG & Co. KGaA).

The dipolyhydroxystearic acid esters of polyhydric alcohols may be used alone or in combination of two or more thereof.

The content of the dipolyhydroxystearic acid ester of a polyhydric alcohol in the water-in-oil emulsified sunscreen cosmetic of the present invention is, from the viewpoint of water resistance, emulsion stability, powder dispersibility, and the like, preferably 0.1 mass % or more, more preferably 0.5 mass % or more, further more preferably 0.75 mass % or more, and particularly preferably 1.2 mass % or more and is, from the viewpoint of water resistance, non-stickiness, easiness to spread, and the like, preferably 10 mass % or less, more preferably 7.5 mass % or less, further more preferably 5 mass % or less, and particularly preferably 3 mass % or less. The specific range in the water-in-oil emulsified sunscreen cosmetic of the present invention is preferably 0.1 mass % or more and 10 mass % or less, more preferably 0.5 mass % or more and 7.5 mass % or less, further more preferably 0.75 mass % or more and 5 mass % or less, and particularly preferably 1.2 mass % or more and 3 mass % or less.

In the water-in-oil emulsified sunscreen cosmetic of the present invention, a mass ratio of the component (B) to the component (A), [(B)/(A)], is 0.01 or more and 0.2 or less.

The mass ratio of the component (B) to the component (A), [(B)/(A)], is, from the viewpoint of water resistance, absence of white residue, emulsion stability, powder dispersibility, and the like, preferably 0.02 or more, more preferably 0.025 or more, further more preferably 0.03 or more, and particularly preferably 0.055 or more and is, from the viewpoint of ultraviolet protection performance, water resistance, non-stickiness, easiness to spread, and the like, preferably 0.15 or less, more preferably 0.125 or less, further more preferably 0.1 or less, and particularly preferably 0.08 or less. The specific range is preferably 0.02 or more and 0.15 or less, more preferably 0.025 or more and 0.125 or less, further more preferably 0.03 or more and 0.1 or less, and particularly preferably 0.055 or more and 0.08 or less.

A mass ratio of the component (B) to the total of surfactants contained in the water-in-oil emulsified sunscreen cosmetic is preferably 0.3 or more, more preferably 0.5 or more, and particularly preferably 0.6 or more and is preferably 1 or less, more preferably 0.9 or less, and particularly preferably 0.75 or less. The specific range is preferably 0.3 or more and 1 or less, more preferably 0.5 or more and 0.9 or less, and particularly preferably 0.6 or more and 0.75 or less.

<Component (C)>

In the present specification, the term "liquid oil agent" means oil agents that are in a liquid state at 25° C. at 1 atm excluding oil-soluble ultraviolet absorbing agents that are in a liquid state at 25° C. at 1 atm.

The liquid oil agent may be a volatile oil agent or a nonvolatile oil agent. In addition, liquid oil agents may be used alone or in combination of two or more. The volatile oil agent is an oil agent showing volatility at 25° C., and the nonvolatile oil agent is an oil agent not showing volatility at 25° C.

Examples of the volatile oil agent include light isoparaffin, octamethylcyclotetrasiloxane, decamethylcyclopentasiloxane, dodecamethylcyclohexasiloxane, methyl trimethicone, decamethyl tetrasiloxane, ethyl trisiloxane, and volatile methylpolysiloxane.

Examples of the commercial product of light isoparaffin include Isopar H (manufactured by Esso Chemical Limited), Isododecane (manufactured by Bayer Corporation), Isohexadecane (manufactured by Uniqema), and IP Solvent 1620MU, IP Solvent 2028MU, and IP Solvent 2835 (all manufactured by Idemitsu Kosan Co., Ltd.). Examples of the commercial product of decamethylcyclopentasiloxane include TSF405 (manufactured by Momentive Performance Materials Japan LLC), SH245 and DC345 (manufactured by DuPont Toray Specialty Materials K.K.), and KF-995 (manufactured by Shin-Etsu Chemical Co., Ltd.). Examples of the commercial product of methyl trimethicone include Silicone TMF-1.5 (manufactured by Shin-Etsu Chemical Co., Ltd.). Examples of the commercial product of decamethyl tetrasiloxane include KF-96L-1.5CS (manufactured by Shin-Etsu Chemical Co., Ltd.). Examples of the commercial product of ethyl trisiloxane include SILSOFTETS (manufactured by Momentive Performance Materials Japan LLC). Examples of the commercial product of volatile methylpolysiloxane include KF-96L-2CS (manufactured by Shin-Etsu Chemical Co., Ltd.).

Examples of the nonvolatile oil agent include liquid paraffins (light liquid paraffin, light liquid isoparaffin, and heavy liquid isoparaffin) and nonvolatile hydrocarbon oils, such as squalane; nonvolatile silicone oils, such as nonvolatile dimethylpolysiloxane and nonvolatile methylphenylpolysiloxane; nonvolatile fatty acid ester oils, such as cetyl 2-ethylhexanoate, isononyl isononanate, isotridecyl isononanate, isopropyl myristate, isopropyl palmitate, 2-ethylhexyl palmitate, 2-ethylhexyl stearate, and stearyl stearate; and C12-15 alkyl benzoates. Examples of the nonvolatile fatty acid ester oil include fatty acid triglyceride, such as glyceryl tri(caprylate/caprate) and glyceryl tri(2-ethylhexanoate); esters of fatty acid and neopentyl glycol, such as neopentyl glycol dicaprate and neopentyl glycol diethylhexanoate; and polyhydric alcohol fatty acid ester oil.

Examples of the commercial product of liquid paraffin include PARLEAM 4 (manufactured by NOF Corporation). Examples of the commercial product of nonvolatile dimethylpolysiloxane include KF-96A-10CS (manufactured by Shin-Etsu Chemical Co., Ltd.). Examples of the commercial product of isopropyl palmitate include EXCEPARL IPP (manufactured by Kao Corporation). Examples of the commercial product of C12-15 alkyl benzoate include FINSOLV TN (manufactured by Innospec Active Chemicals LLC). Examples of the commercial product of neopentyl glycol dicaprate include ESTEMOL N-01 (manufactured by The Nisshin OilliO Group, Ltd.).

A content of the liquid oil agent in the water-in-oil emulsified sunscreen cosmetic of the present invention is 35 mass % or more and 85 mass % or less. When the content of the liquid oil agent is 35 mass % or more, the water resistance and the easiness to spread are improved.

The content of the liquid oil agent in the water-in-oil emulsified sunscreen cosmetic of the present invention is, from the viewpoint of easiness to spread, and the like, preferably 40 mass % or more, more preferably 45 mass % or more, further more preferably 47.5 mass % or more, and particularly preferably 50 mass % or more and is, from the viewpoint of non-stickiness, dripping property, and the like, preferably 80 mass % or less, more preferably 70 mass % or less, further more preferably 65 mass % or less, and particularly preferably 60 mass % or less. The specific range in the water-in-oil emulsified sunscreen cosmetic of the present invention is preferably 40 mass % or more and 80 mass % or less, more preferably 45 mass % or more and 70 mass % or less, further more preferably 47.5 mass % or more and 65 mass % or less, and particularly preferably 50 mass % or more and 60 mass % or less.

A mass ratio of the component (A) to the component (C), [(A)/(C)], is, from the viewpoint of ultraviolet protection performance, dripping property, and the like, preferably 0.03 or more, more preferably 0.1 or more, and particularly preferably 0.3 or more and is, from the viewpoint of powder dispersibility, easiness to spread, and the like, preferably 2 or less, more preferably 1.5 or less, and particularly preferably 1 or less. The specific range is preferably 0.03 or more and 2 or less, more preferably 0.1 or more and 1.5 or less, and particularly preferably 0.3 or more and 1 or less.

A mass ratio of the component (B) to the component (C), [(B)/(C)], is, from the viewpoint of ultraviolet protection performance, water resistance, emulsion stability, and the like, preferably 0.001 or more, more preferably 0.003 or more, further more preferably 0.01 or more, and particularly preferably 0.03 or more and is, from the viewpoint of water resistance, non-stickiness, and the like, preferably 0.15 or less, more preferably 0.1 or less, and further more preferably 0.05 or less. The specific range is preferably 0.001 or more and 0.15 or less, more preferably 0.003 or more and 0.1 or less, further more preferably 0.01 or more and 0.1 or less, and particularly preferably 0.03 or more and 0.05 or less.

<Component (D)>

The water-in-oil emulsified sunscreen cosmetic of the present invention contains (D) water.

The content of water in the water-in-oil emulsified sunscreen cosmetic of the present invention is, from the viewpoint of dripping property, emulsion stability, and the like, preferably 0.1 mass % or more, more preferably 0.5 mass % or more, further more preferably 1 mass % or more, and particularly preferably 1.5 mass % or more and is, from the viewpoint of water resistance, easiness to spread, ultraviolet protection performance, and the like, preferably 25 mass % or less, more preferably 20 mass % or less, further more preferably 15 mass % or less, and particularly preferably 10 mass % or less. The specific range in the water-in-oil emulsified sunscreen cosmetic of the present invention is preferably 0.1 mass % or more and 25 mass % or less, more preferably 0.5 mass % or more and 20 mass % or less, further more preferably 1 mass % or more and 15 mass % or less, and particularly preferably 1.5 mass % or more and 10 mass % or less.

A mass ratio of the component (D) to the component (C), [(D)/(C)], is, from the viewpoint of non-stickiness, emulsion stability, and the like, preferably 0.005 or more, more preferably 0.01 or more, further more preferably 0.02 or more, and particularly preferably 0.04 or more and is, from the viewpoint of water resistance, emulsion stability, and the like, preferably 1 or less, more preferably 0.5 or less, further more preferably 0.25 or less, and particularly preferably 0.125 or less. The specific range is preferably 0.005 or more and 1 or less, more preferably 0.01 or more and 0.5 or less, further more preferably 0.02 or more and 0.25 or less, and particularly preferably 0.04 or more and 0.125 or less.

The water-in-oil emulsified sunscreen cosmetic of the present invention, from the viewpoint of ultraviolet protection performance, water resistance, abrasion resistance, smoothness, moisturizing feeling, powder dispersibility, emulsion stability, and the like, preferably further contains one or more selected from the group consisting of (E) an alkyl modified silicone wax having a melting point of 60° C. or more, (F) a surfactant other than the component (B), and (G) polyhydric alcohol, in addition to the components (A) to (D), and more preferably contains the components (A) to (E) or the components (A) to (D) and (F), further more preferably contains the components (A) to (F), and particularly preferably contains the components (A) to (G). When the component (E) is further contained in addition to the components (A) to (D), the ultraviolet protection performance, the water resistance, the abrasion resistance, the smoothness, the moisturizing feeling, and the like are further improved. When the component (F) is further contained in addition to the components (A) to (D), the water resistance, the powder dispersibility, the emulsion stability, and the like are further improved.

<Component (E)>

The alkyl modified silicone wax having a melting point of 60° C. or more is, from the viewpoint of ultraviolet protection performance, water resistance, non-stickiness, and the like, preferably a wax having a melting point of 60° C. or more in which dimethyl silicone is modified with an alkyl group having from 9 to 80 carbon atoms.

The above alkyl group may be linear or branched. The number of carbon atoms of the alkyl group is preferably 16 or more, more preferably 20 or more, and particularly preferably 24 or more and is preferably 70 or less, more preferably 60 or less, and particularly preferably 50 or less. The specific range is preferably 16 or more and 70 or less, more preferably 20 or more and 60 or less, and particularly preferably 24 or more and 50 or less.

The site of substitution of this alkyl group is arbitrary, and the form of substitution may be any one of one-end type, both-end type, side-chain type, and the like. The number of substitutions of the alkyl group is also arbitrary and may be one or more in a single molecule. When the number of substitution of the alkyl group is two or more, the two or more alkyl groups may be the same or different. Incidentally, a mixture of silicone waxes modified different alkyl groups may be used.

The melting point of the alkyl modified silicone wax as the component (E) is 60° C. or more and is preferably 61° C. or more and more preferably 62° C. or more and is preferably 120° C. or less, more preferably 90° C. or less, and particularly preferably 80° C. or less. The specific range is preferably 60° C. or more and 90° C. or less, more preferably 61° C. or more and 80° C. or less, and particularly preferably 62° C. or more and 80° C. or less.

In the present specification, the melting point means a melting point measured in accordance with JIS K0064.

As the alkyl modified silicone wax having a melting point of 60° C. or more, an oil-soluble alkyl modified silicone wax having a melting point of 60° C. or more is preferable.

Examples of the alkyl modified silicone wax having a melting point of 60° C. or more include an alkyl methicone wax having a melting point of 60° C. or more, an alkyl dimethicone wax having a melting point of 60° C. or more, and a silsesquioxane resin wax having a melting point of 60° C. or more, and these waxes may be used alone or in combination of two or more thereof. Among these waxes, from the viewpoint of smoothness, non-stickiness, and the like, the alkyl methicone wax having a melting point of 60° C. or more and the silsesquioxane resin wax having a melting point of 60° C. or more are preferable.

The alkyl modified silicone wax having a melting point of 60° C. or more may be a commercially available one or may be synthesized in accordance with a conventional method. For example, C26-28 alkyl methicone (BELSIL CM 7026 VP, manufactured by Wacker Asahikasei Silicone Co., Ltd., melting point: 70° C.), C30-45 alkyl methicone (AMS-C30 Cosmetic Wax, manufactured by DuPont Toray Specialty Materials K.K., melting point: 73° C. to 77° C.), C30-45 alkyl dimethicone (SF-1642, manufactured by Momentive Performance Materials Japan LLC, melting point: 60° C. to 70° C.), and C30-45 alkyldimethylsilyl polypropylsilsesquioxane (SW-8005 C30 Resin Wax, manufactured by DuPont Toray Specialty Materials K.K., melting point: 63° C. to 71° C.) are mentioned.

The alkyl modified silicone waxes having a melting point of 60° C. or more may be used alone or in combination of two or more thereof.

The content of the alkyl modified silicone wax having a melting point of 60° C. or more in the water-in-oil emulsified sunscreen cosmetic of the present invention is, from the viewpoint of ultraviolet protection performance, water resistance, abrasion resistance, smoothness, and the like, preferably 0 mass % or more, more preferably 0.05 mass % or more, further more preferably 0.1 mass % or more, and particularly preferably 0.4 mass % or more and is, from the viewpoint of absence of white residue, easiness to spread, and the like, preferably 12 mass % or less, more preferably 8 mass % or less, further more preferably 4 mass % or less, and particularly preferably 2 mass % or less. The specific range in the water-in-oil emulsified sunscreen cosmetic of the present invention is preferably 0 mass % or more and 12 mass % or less, more preferably 0.05 mass % or more and 8 mass % or less, further more preferably 0.1 mass % or more and 4 mass % or less, and particularly preferably 0.4 mass % or more and 2 mass % or less.

When the content of the alkyl modified silicone wax having a melting point of 60° C. or more is 2 mass % or less, absence of white residue and easiness to spread are particularly improved.

A mass ratio of the component (E) to the component (A), [(E)/(A)], is, from the viewpoint of water resistance, abrasion resistance, non-stickiness, and the like, preferably 0.001 or more, more preferably 0.003 or more, further more preferably 0.009 or more, and particularly preferably 0.027 or more and is, from the viewpoint of ultraviolet protection performance, easiness to spread, and the like, preferably 5.4 or less, more preferably 1.8 or less, further more preferably 0.6 or less, and particularly preferably 0.2 or less. The specific range is preferably 0.001 or more and 5.4 or less, more preferably 0.003 or more and 1.8 or less, further more preferably 0.009 or more and 0.6 or less, and particularly preferably 0.027 or more and 0.2 or less.

<Component (F)>

The surfactant other than the component (B) may be a known surfactant, such as an anionic surfactant, a cationic surfactant, a nonionic surfactant, and an amphoteric surfactant, and is, from the viewpoint of water resistance, ease of mixing, and the like, preferably a nonionic surfactant other than the component (B) and more preferably a nonionic surfactant having an HLB of 8 or less (preferably an HLB of from 1 to 7, more preferably an HLB of from 2 to 6, and particularly preferably an HLB of from 3 to 5) other than the component (B). The surfactant is preferably in a liquid state at 25° C.

Here, the HLB is an indicator showing hydrophile-lipophile balance and is defined by the following expression by Oda, Teramura, et al.

$$HLB=(\Sigma(\text{inorganicity value})/\Sigma(\text{organicity value}))\times 10$$

Examples of the nonionic surfactant other than the component (B) include polyhydric alcohol fatty acid ester surfactants, polyether modified silicone surfactants, and polyoxyethylene alkyl ether surfactants. Among these surfactants, from the viewpoint of water resistance, powder dispersibility, and the like, the polyhydric alcohol fatty acid ester surfactants are preferable, a glycerol fatty acid ester surfactant, a sorbitan fatty acid ester surfactant, a diglycerol fatty acid ester surfactant, a polyglycerol fatty acid ester surfactant, and a propylene glycol fatty acid ester surfactant are more preferable, a sorbitan fatty acid ester surfactant is further more preferable, and a sorbitan mono-fatty acid ester surfactant is particularly preferable.

Although the fatty acid residue of the polyhydric alcohol fatty acid ester surfactant is a non-polymer, it may be either a saturated fatty acid residue or an unsaturated fatty acid residue and may be a linear fatty acid residue or a branched fatty acid residue. The number of the fatty acid residues in a molecule of the polyhydric alcohol fatty acid ester surfactant is, although it depends on the type of the polyhydric alcohol, preferably from 1 to 3.

The number of carbon atoms of the fatty acid residue is preferably from 8 to 24, more preferably from 12 to 22, and particularly preferably from 14 to 20.

Examples of the polyhydric alcohol fatty acid ester surfactant include glyceryl myristate, glyceryl stearate, glyceryl isostearate, glyceryl oleate, sorbitan monostearate, sorbitan monoisostearate, sorbitan monooleate, sorbitan tristearate, sorbitan trioleate, diglyceryl monostearate, diglyceryl monoisostearate, diglyceryl monooleate, tetraglyceryl monostearate, hexaglyceryl tristearate, decaglyceryl pentastearate, decaglyceryl pentaisostearate, decaglyceryl pentaoleate, and propylene glycol monostearate. Among these surfactants, from the viewpoint of water resistance, absence of white residue, emulsion stability, powder dispersibility, and the like, sorbitan monoisostearate is preferable.

The surfactants other than the component (B) may be used alone or in combination of two or more thereof.

The content of the surfactant other than the component (B) in the water-in-oil emulsified sunscreen cosmetic of the present invention is, from the viewpoint of water resistance, powder dispersibility, and the like, preferably 0 mass % or more, more preferably 0.1 mass % or more, and particularly preferably 0.5 mass % or more and is, from the viewpoint of water resistance, powder dispersibility, and the like, preferably 10 mass % or less, more preferably 5 mass % or less, further more preferably 2.5 mass % or less, and particularly preferably 2 mass % or less. The specific range in the water-in-oil emulsified sunscreen cosmetic of the present invention is preferably 0 mass % or more and 10 mass % or less, more preferably 0.1 mass % or more and 5 mass % or less, further more preferably 0.5 mass % or more and 2.5 mass % or less, and particularly preferably 0.5 mass % or more and 2 mass % or less.

A mass ratio of the component (F) to the component (B), [(F)/(B)], is, from the viewpoint of water resistance, powder dispersibility, and the like, preferably 0.05 or more, more preferably 0.1 or more, and particularly preferably 0.25 or more and is, from the viewpoint of water resistance, powder dispersibility, and the like, preferably 2 or less, more preferably 1 or less, and particularly preferably 0.5 or less. The specific range is preferably 0.05 or more and 2 or less, more preferably 0.1 or more and 1 or less, and particularly preferably 0.25 or more and 0.5 or less.

<Component (G)>

Examples of the polyhydric alcohol include glycols and glycerols. Examples of the glycols include alkylene glycol, such as ethylene glycol, propylene glycol, and 1,3-butylene glycol; dialkylene glycol, such as diethylene glycol and dipropylene glycol; and polyalkylene glycol, such as polyethylene glycol and polypropylene glycol. Examples of the glycerols include glycerol, diglycerol, and polyglycerol.

The polyhydric alcohols may be used alone or in combination of two or more thereof.

The content of the polyhydric alcohol in the water-in-oil emulsified sunscreen cosmetic of the present invention, from the viewpoint of ultraviolet protection performance and moisturizing feeling, preferably 0 mass % or more and 20 mass % or less, more preferably 2 mass % or more and 15 mass % or less, and particularly preferably 4 mass % or more and 10 mass % or less.

The water-in-oil emulsified sunscreen cosmetic of the present invention may contain, for example, an oily thickener other than the component (E), waxes other than the component (E), a powder other than the component (A), a lower alcohol, a preservative, a perfume, a pH adjuster, a moisturizing agent, a film-forming agent, a texture improver, a sebum absorber, and a viscosity modifier, in addition to the above-mentioned components. These ingredients may be used alone or in combination of two or more thereof.

Examples of the oily thickener other than the component (E) include polyglyceryl isostearate, inulin fatty acid ester, dextrin fatty acid ester, an organically modified clay mineral, and glyceryl (behenate/eicosadioate). These thickeners may be used alone or in combination of two or more thereof.

The content of the oily thickener other than the component (E) in the water-in-oil emulsified sunscreen cosmetic of the present invention is preferably 0 mass % or more and 1 mass % or less and more preferably 0 mass % or more and 0.5 mass % or more.

Examples of the powder other than the component (A) include hydrophobized talc, cellulose particles, porous silica, crosslinked (meth)acrylic acid ester resin particles, and silicone resin particles. These powders may be used alone or in combination of two or more thereof.

The content of the powder other than the component (A) in the water-in-oil emulsified sunscreen cosmetic of the present invention is preferably 0 mass % or more and 5 mass % or less and more preferably 0 mass % or more and 3 mass % or less.

Examples of the dosage form of the water-in-oil emulsified sunscreen cosmetic of the present invention include non-solid forms, such as liquid, milky liquid, cream, and multi-layer forms, and a multi-layer form is preferable. In the present specification, the term "multi-layer water-in-oil emulsified cosmetic" refers to a cosmetic that is a multi-layer type at least including two layers of a water layer and an oil layer, has an appearance in which the water layer and the oil layer are separated into multiple layers when left to stand before use, and is used as a water-in-oil milky liquid by lightly shaking immediately before use. In the present specification, the "water-in-oil emulsified sunscreen cosmetic" includes both one that becomes a water-in-oil milky liquid when shaken and one that is a water-in-oil milky liquid both when left to stand and when shaken.

The viscosity at 25° C. of the water-in-oil emulsified sunscreen cosmetic of the present invention is, from the viewpoint of ease of application, dripping property, and the like, preferably 30 mPa·s or more, more preferably 100 mPa·s or more, further more preferably 300 mPa·s or more, and particularly preferably 500 mPa·s or more and is, from the viewpoint of ease of application, easiness to spread, absence of white residue, and the like, preferably 15,000 mPa·s or less, more preferably 10,000 mPa·s or less, further more preferably 5,000 mPa·s or less, and particularly preferably 3,000 mPa·s or less. The specific range is preferably 30 mPa·s or more and 15,000 mPa·s or less, more preferably 100 mPa·s or more and 10,000 mPa·s or less, further more preferably 300 mPa·s or more and 5,000 mPa·s or less, and particularly preferably 500 mPa·s or more and 3,000 mPa·s or less.

The above-mentioned viscosity at 25° C. can be measured with a Brookfield viscometer (B-type viscometer, specifically, the viscosity may be measured on the following day of preparation by the method described in examples.

The water-in-oil emulsified sunscreen cosmetic of the present invention can be used as a sunscreen by being applied to the skin (preferably to the skin excluding the scalp, more preferably to the face, body, limbs, and the like). Although the method of application is not particularly limited, it is preferable to apply the water-in-oil emulsified sunscreen cosmetic by hand or by an application tool.

The water-in-oil emulsified sunscreen cosmetic of the present invention can be manufactured in accordance with a conventional method.

The water-in-oil emulsified sunscreen cosmetic of the present invention is easy to spread while applying and is unlikely to decrease the SPF value when the applied site is wet with water although containing a high content of the hydrophobized ultraviolet scattering agent. In addition, in spite of a high content of the hydrophobized ultraviolet scattering agent, white residue after application is also unlikely to occur.

Here, although the reason why the SPF value is unlikely to decrease even when the applied site is wet with water is not necessarily clear, it is inferred that the hydrophobized ultraviolet scattering agent maintains the dispersibility even when wet with water and is unlikely to aggregate and is thereby prevented from remaining in the recesses, such as skin groove and pores, of the skin texture.

The water-in-oil emulsified sunscreen cosmetic of the present invention can obtain high ultraviolet protection performance even when the content of the ultraviolet absorbing agent is reduced or even when the ultraviolet absorbing agent is not used. The content of the ultraviolet absorbing agent in the water-in-oil emulsified sunscreen cosmetic of the present invention is preferably 0 mass % or more and 5 mass % or less, more preferably 0 mass % or more and 2.5 mass % or less, further more preferably 0 mass % or more and 1 mass % or less, further more preferably 0 mass % or more and 0.5 mass % or less, and particularly preferably 0 mass %.

The present invention further discloses the following cosmetics and the like, relating the above-described embodiments.

<1> A water-in-oil emulsified sunscreen cosmetic containing the following components (A), (B), (C), and (D):

(A) 10 mass % or more and 50 mass % or less of a hydrophobized ultraviolet scattering agent, (B) a dipolyhydroxystearic acid ester of a polyhydric alcohol, (C) 35 mass % or more and 85 mass % or less of a liquid oil agent, and (D) water;

wherein a mass ratio of the component (B) to the component (A), [(B)/(A)], is 0.01 or more and 0.2 or less.

<2> The water-in-oil emulsified sunscreen cosmetic according to <1>, wherein the component (A) is preferably a hydrophobized fine particle metal oxide, more preferably one or more fine particle metal oxides selected from the group consisting of zinc oxide, titanium oxide, cerium oxide, iron oxide, and chromium oxide and subjected to hydrophobization treatment, further more preferably one or more fine particle metal oxides selected from the group consisting of zinc oxide, titanium oxide, and cerium oxide and subjected to hydrophobization treatment, and particularly preferably one or more fine particle metal oxides selected from the group consisting of zinc oxide and titanium oxide and subjected to hydrophobization treatment.

<3> The water-in-oil emulsified sunscreen cosmetic according to <1> or <2>, wherein the hydrophobization treatment of the component (A) is preferably hydrophobization treatment selected from the group consisting of fluorine compound treatment, silicone treatment, silicone resin treatment, pendant treatment, silane coupling agent treatment, titanium coupling agent treatment, oil agent treatment, N-acylated lysine treatment, polyacrylic acid treatment, metal soap treatment, amino acid treatment, inorganic compound treatment, plasma treatment, mechanochemical treatment, silane compound treatment, and silazane compound treatment and more preferably hydrophobization treatment selected from the group consisting of silicone treatment, silicone resin treatment, silane compound treatment, silazane compound treatment, and metal soap treatment.

<4> The water-in-oil emulsified sunscreen cosmetic according to any one of <1> to <3>, wherein the content of the component (A) in the water-in-oil emulsified sunscreen cosmetic is preferably 12.5 mass % or more, more preferably 15 mass % or more, further more preferably 20 mass % or more, and particularly preferably 22.5 mass % or more and is 50 mass % or less, preferably 40 mass % or less, more preferably 35 mass % or less, and further more preferably 32.5 mass % or less.

<5> The water-in-oil emulsified sunscreen cosmetic according to any one of <1> to <3>, wherein the content of the component (A) in the water-in-oil emulsified sunscreen cosmetic is preferably 12.5 mass % or more and 50 mass % or less, more preferably 15 mass % or more and 40 mass % or less, further more preferably 20 mass % or more and 35 mass % or less, and particularly preferably 22.5 mass % or more and 32.5 mass % or less.

<6> The water-in-oil emulsified sunscreen cosmetic according to any one of <1> to <5>, wherein the component (B) is preferably a compound in which polyhydroxystearic acid is ester-bonded to each of two hydroxy groups of glycols or glycerols, more preferably a compound in which polyhydroxystearic acid is ester-bonded to each of two hydroxy groups of dialkylene glycol, polyalkylene glycol, diglycerol, or polyglycerol, further more preferably a compound in which polyhydroxystearic acid is ester-bonded to each of two hydroxy groups of polyalkylene glycol, and further more preferably a compound in which polyhydroxystearic acid is ester-bonded to each of two hydroxy groups of polyethylene glycol.

<7> The water-in-oil emulsified sunscreen cosmetic according to any one of <1> to <5>, wherein the component (B) is preferably one or more selected from the group consisting of polyalkylene glycol dipolyhydroxystearate and polyglyceryl-2 dipolyhydroxystearate, more preferably polyalkylene glycol dipolyhydroxystearate, further more preferably polyethylene glycol dipolyhydroxystearate, and particularly preferably polyethylene glycol (30) dipolyhydroxystearate.

<8> The water-in-oil emulsified sunscreen cosmetic according to any one of <1> to <7>, wherein the content of the component (B) in the water-in-oil emulsified sunscreen cosmetic is preferably 0.1 mass % or more, more preferably 0.5 mass % or more, further more preferably 0.75 mass % or more, and particularly preferably 1.2 mass % or more and is preferably 10 mass % or less, more preferably 7.5 mass % or less, further more preferably 5 mass % or less, and particularly preferably 3 mass % or less.

<9> The water-in-oil emulsified sunscreen cosmetic according to any one of <1> to <7>, wherein the content of the component (B) in the water-in-oil emulsified sunscreen cosmetic is preferably 0.1 mass % or more and 10 mass % or less, more preferably 0.5 mass % or more and 7.5 mass % or less, further more preferably 0.75 mass % or more and 5 mass % or less, and particularly preferably 1.2 mass % or more and 3 mass % or less.

<10> The water-in-oil emulsified sunscreen cosmetic according to any one of <1> to <9>, wherein the mass ratio of the component (B) to the component (A), [(B)/(A)], is preferably 0.02 or more, more preferably 0.025 or more, further more preferably 0.03 or more, and particularly preferably 0.055 or more and is preferably 0.15 or less, more preferably 0.125 or less, further more preferably 0.1 or less, and particularly preferably 0.08 or less.

<11> The water-in-oil emulsified sunscreen cosmetic according to any one of <1> to <9>, wherein the mass ratio of the component (B) to the component (A), [(B)/(A)], is preferably 0.02 or more and 0.15 or less, more preferably 0.025 or more and 0.125 or less, further more preferably 0.03 or more and 0.1 or less, and particularly preferably 0.055 or more and 0.08 or less.

<12> The water-in-oil emulsified sunscreen cosmetic according to any one of <1> to <11>, wherein the component (C) is preferably one or more selected from the group consisting of light isoparaffin, octamethylcyclotetrasiloxane, decamethylcyclopentasiloxane, dodecamethylcyclohexasiloxane, methyl trimethicone, decamethyl tetrasiloxane, ethyl trisiloxane, volatile methylpolysiloxane, nonvolatile hydrocarbon oils, nonvolatile silicone oil, nonvolatile fatty acid ester oil, and C12-15 alkyl benzoate, and more preferably one or more selected from the group consisting of light isoparaffin, octamethylcyclotetrasiloxane, decamethylcyclopentasiloxane, dodecamethylcyclohexasiloxane, methyl trimethicone, decamethyl tetrasiloxane, ethyl trisiloxane, volatile methylpolysiloxane, liquid paraffin, squalane, nonvolatile dimethylpolysiloxane, nonvolatile methylphenylpolysiloxane, cetyl 2-ethylhexanoate, isononyl isononanate, isotridecyl isononanate, isopropyl myristate, isopropyl palmitate, 2-ethylhexyl palmitate, 2-ethylhexyl stearate, stearyl stearate, fatty acid triglyceride, esters of fatty acid and neopentyl glycol, polyhydric alcohol fatty acid ester oil, and C12-15 alkyl benzoate.

<13> The water-in-oil emulsified sunscreen cosmetic according to any one of <1> to <12>, wherein the content of the component (C) in the water-in-oil emulsified sunscreen cosmetic is preferably 40 mass % or more, more preferably 45 mass % or more, further more preferably 47.5 mass % or more, and particularly preferably 50 mass % or more and is preferably 80 mass % or less, more preferably 70 mass % or less, further more preferably 65 mass % or less, and particularly preferably 60 mass % or less.

<14> The water-in-oil emulsified sunscreen cosmetic according to any one of <1> to <12>, wherein the content of the component (C) in the water-in-oil emulsified sunscreen cosmetic is preferably 40 mass % or more and 80 mass % or less, more preferably 45 mass % or more and 70 mass % or less, further more preferably 47.5 mass % or more and 65 mass % or less, and particularly preferably 50 mass % or more and 60 mass % or less.

<15> The water-in-oil emulsified sunscreen cosmetic according to any one of <1> to <14>, wherein a mass ratio of the component (A) to the component (C), [(A)/(C)], is preferably 0.03 or more, more preferably 0.1 or more, and particularly preferably 0.3 or more and is preferably 2 or less, more preferably 1.5 or less, and particularly preferably 1 or less.

<16> The water-in-oil emulsified sunscreen cosmetic according to any one of <1> to <15>, wherein a mass ratio of the component (B) to the component (C), [(B)/(C)], is preferably 0.001 or more, more preferably 0.003 or more, further more preferably 0.01 or more, and particularly preferably 0.03 or more and is preferably 0.15 or less, more preferably 0.1 or less, and further more preferably 0.05 or less.

<17> The water-in-oil emulsified sunscreen cosmetic according to any one of <1> to <16>, wherein the content of the component (D) in the water-in-oil emulsified sunscreen cosmetic is preferably 0.1 mass % or more, more preferably 0.5 mass % or more, further more preferably 1 mass % or more, and particularly preferably 1.5 mass % or more and is preferably 25 mass % or less, more preferably 20 mass % or less, further more preferably 15 mass % or less, and particularly preferably 10 mass % or less.

<18> The water-in-oil emulsified sunscreen cosmetic according to any one of <1> to <16>, wherein the content of the component (D) in the water-in-oil emulsified sunscreen cosmetic is preferably 0.1 mass % or more and 25 mass % or less, more preferably 0.5 mass % or more and 20 mass % or less, further more preferably 1 mass % or more and 15 mass % or less, and particularly preferably 1.5 mass % or more and 10 mass % or less.

<19> The water-in-oil emulsified sunscreen cosmetic according to any one of <1> to <18>, wherein a mass ratio of the component (D) to the component (C), [(D)/(C)], is preferably 0.005 or more, more preferably 0.01 or more, further more preferably 0.02 or more, and particularly preferably 0.04 or more and is preferably 1 or less, more preferably 0.5 or less, further more preferably 0.25 or less, and particularly preferably 0.125 or less.

<20> The water-in-oil emulsified sunscreen cosmetic according to any one of <1> to <19> further containing (E) an alkyl modified silicone wax having a melting point of 60° C. or more.

<21> The water-in-oil emulsified sunscreen cosmetic according to <20>, wherein the alkyl modified silicone wax as the component (E) preferably has a melting point of 61° C. or more and more preferably 62° C. or more and has preferably 120° C. or less, more preferably 90° C. or less, and particularly preferably 80° C. or less.

<22> The water-in-oil emulsified sunscreen cosmetic according to <20> or <21>, wherein the component (E) is preferably an oil-soluble alkyl modified silicone wax having a melting point of 60° C. or more, more preferably one or more selected from the group consisting of an alkyl methicone wax having a melting point of 60° C. or more, an alkyl dimethicone wax having a melting point of 60° C. or more, and a silsesquioxane resin wax having a melting point of 60° C. or more, and particularly preferably one or more selected from the group consisting of an alkyl methicone wax having a melting point of 60° C. or more and a silsesquioxane resin wax having a melting point of 60° C. or more.

<23> The water-in-oil emulsified sunscreen cosmetic according to any one of <20> to <22>, wherein the content of the component (E) in the water-in-oil emulsified sunscreen cosmetic is preferably 0 mass % or more, more preferably 0.05 mass % or more, further more preferably 0.1 mass % or more, and particularly preferably 0.4 mass % or more and is preferably 12 mass % or less, more preferably 8 mass % or less, further more preferably 4 mass % or less, and particularly preferably 2 mass % or less.

<24> The water-in-oil emulsified sunscreen cosmetic according to any one of <1> to <23> further containing (F) a surfactant other than the component (B).

<25> The water-in-oil emulsified sunscreen cosmetic according to <24>, wherein the component (F) is preferably a nonionic surfactant other than the component (B), more preferably one or more selected from the group consisting of a polyhydric alcohol fatty acid ester surfactant, a polyether modified silicone surfactant, and a polyoxyethylene alkyl ether surfactant, further more preferably a polyhydric alcohol fatty acid ester surfactant, further more preferably one or more selected from the group consisting of a glycerol fatty acid ester surfactant, a sorbitan fatty acid ester surfactant, a diglycerol fatty acid ester surfactant, a polyglycerol fatty acid ester surfactant, and a propylene glycol fatty acid ester surfactant, further more preferably a sorbitan fatty acid ester surfactant, further more preferably a sorbitan mono-fatty acid ester surfactant, and particularly preferably sorbitan monoisostearate.

<26> The water-in-oil emulsified sunscreen cosmetic according to <24> or <25>, wherein the content of the component (F) in the water-in-oil emulsified sunscreen cosmetic is preferably 0 mass % or more, more preferably 0.1 mass % or more, and particularly preferably 0.5 mass % or more and is preferably 10 mass % or less, more preferably 5 mass % or less, further more preferably 2.5 mass % or less, and particularly preferably 2 mass % or less.

<27> The water-in-oil emulsified sunscreen cosmetic according to any one of <1> to <26>, further containing (G) a polyhydric alcohol.

<28> The water-in-oil emulsified sunscreen cosmetic according to <27>, wherein the component (G) is preferably one or more selected from the group consisting of glycols and glycerols, more preferably one or more selected from the group consisting of alkylene glycol, dialkylene glycol, polyalkylene glycol, glycerol, diglycerol, and polyglycerol, and further more preferably one or more selected from the group consisting of ethylene glycol, propylene glycol, 1,3-butylene glycol, diethylene glycol, dipropylene glycol, polyethylene glycol, polypropylene glycol, glycerol, diglycerol, and polyglycerol.

<29> The water-in-oil emulsified sunscreen cosmetic according to <27> or <28>, wherein the content of the component (G) in the water-in-oil emulsified sunscreen cosmetic is preferably 0 mass % or more and 20 mass % or less, more preferably 2 mass % or more and 15 mass % or less, and particularly preferably 4 mass % or more and 10 mass % or less.

<30> The water-in-oil emulsified sunscreen cosmetic according to any one of <1> to <29>, further containing one or more selected from the group consisting of an oily thickener other than the component (E), a wax other than the component (E), a powder other than the component (A), a lower alcohol, a preservative, a perfume, a pH adjuster, a moisturizing agent, a film-forming agent, a texture improver, a sebum absorber, and a viscosity modifier.

<31> The water-in-oil emulsified sunscreen cosmetic according to any one of <1> to <30>, wherein a dosage form of the cosmetic is preferably a liquid, milky liquid, cream, or multi-layer form and more preferably a multi-layer form.

<32> The water-in-oil emulsified sunscreen cosmetic according to any one of <1> to <31>, wherein the viscosity at 25° C. is preferably 30 mPa·s or more, more preferably 100 mPa·s or more, further more preferably 300 mPa·s or more, and particularly preferably 500 mPa·s or more and preferably 15,000 mPa·s or less, more preferably 10,000 mPa·s or less, further more preferably 5,000 mPa·s or less, and particularly preferably 3,000 mPa·s or less.

<33> The water-in-oil emulsified sunscreen cosmetic according to any one of <1> to <32>, wherein the content of the ultraviolet absorbing agent in the water-in-oil emulsified sunscreen cosmetic is preferably 0 mass % or more and 5 mass % or less, more preferably 0 mass % or more and 2.5 mass % or less, further more preferably 0 mass % or more and 1 mass % or less, further more preferably 0 mass % or more and 0.5 mass % or less, and particularly preferably 0 mass %.

EXAMPLES

The present invention will now be described in detail with reference to Examples but is not limited to the Examples. In the Examples, various measurements and evaluations were performed by the following methods.

Measurement Method and Evaluation Method (1) Viscosity

Each cosmetic was filled in a glass bottle with a lid, and the viscosity was measured at 25° C. on the following day of the preparation. In the measurement, a B-type viscometer (TVB-10M) manufactured by Toki Sangyo Co., Ltd. was used, and the viscosity was measured after stirring the inside of the glass bottle in advance at conditions of the rotor: No. 2, the number of rotations: 6 rpm, and the measurement time: 1 minute. When the viscosity is higher than the measuring upper limit, the rotor: No. 3 or No. 4 was used, and the measurement was similarly performed as in above at conditions of the number of rotations: 6 rpm and the measurement time: 1 minute.

(2) SPF

Each cosmetic (18.7 mg) was uniformly applied to Helio-Plates HD6 (manufactured by Labsphere, Inc.) at 0.85 $mg/cm^2$ and was dried for 15 minutes. Then, the SPF value was measured using an SPF analyzer (UV-2000S, manufactured by Labsphere, Inc.).

(3) Water Resistance

Each cosmetic (14.0 mg) was uniformly applied to Helio-Plates HD6 (manufactured by Labsphere, Inc.) at 0.63 $mg/cm^2$ and was dried for 15 minutes. Then, the SPF value was measured using an SPF analyzer (UV-2000S, manufactured by Labsphere, Inc.).

Subsequently, 1.5 mL of water droplets were dropped on the SPF measurement portion of the plate and were left to stand for 80 minutes. The water droplets remained on the plate were then removed with an air duster, and the SPF value was then measured again. The proportion (%) of the SPF value after dropping of water to the SPF value before the dropping defined as 100% was evaluated as water resistance.

(4) Sensory Evaluation (4-1) Easiness to Spread

Easiness to spread while applying was sensorily evaluated by ten expert panelists. The evaluation criteria are shown below:

A: 10 of the panelists answered that it was easy to spread;

B: 7 to 9 of the panelists answered that it was easy to spread;

C: 4 to 6 of the panelists answered that it was easy to spread;

D: 1 to 3 of the panelists answered that it was easy to spread; and

E: None of the panelists answered that it was easy to spread.

(4-2) Absence of white residue on skin

Absence of white residue on skin after application was sensorily evaluated by ten expert panelists. The evaluation criteria are shown below. Here, the term "absence of white residue on skin" means nonuniformity giving white streaks in the application direction.

A: 10 of the panelists answered that there was almost no white residue on skin;

B: 7 to 9 of the panelists answered that there was almost no white residue on skin;

C: 4 to 6 of the panelists answered that there was almost no white residue on skin;

D: 1 to 3 of the panelists answered that there was almost no white residue on skin; and E: None of the panelists answered that there was almost no white residue on skin.

Examples 1 to 13 and Comparative Examples 1 to 5

Water-in-oil emulsified sunscreen cosmetics of Examples 1 to 13 and Comparative Examples 1 to 5 were manufactured by a conventional method in accordance with the prescriptions shown in Tables 1 to 4, and the viscosity and the SPF were measured, and the water resistance and the impression from use were evaluated. Since the cosmetics of Examples 1 to 13 and Comparative Examples 1 to 5 were double layer cosmetics, shaking was performed immediately before the measurements and the evaluations. The results are shown in Tables 1 to 4.

(5) Adhesion Condition of Cosmetic after Wetting with Water

The cosmetics of Example 4 and Comparative Example 3 were also evaluated for the adhesion conditions of the cosmetics after wetting with water, in addition to each of the measurements and evaluations above.

That is, the cosmetic of Example 4 or Comparative Example 3 was applied to an area of 3 cm×3 cm inside the forearm at 2 $mg/cm^2$ and was dried at room temperature for 15 minutes. Subsequently, the applied site was immersed in a water bath for 10 minutes and then was dried at room temperature for 15 minutes again. The applied site was directly observed at a magnification of 40 times using a digital microscope (KH-8700, manufactured by Hirox Co., Ltd.), and the adhesion condition of the powder component (component (A)) on the skin was evaluated by the following criteria. The results thereof were that the cosmetic of Example 4 was rated as "4" and the cosmetic of Comparative Example 3 was rated as "1".

4: No aggregation of the component (A) was observed in the skin texture;

3: Aggregation of the component (A) was slightly observed in the skin texture;

2: Aggregation of the component (A) was observed in the skin groove of the skin texture; and 1: Aggregation of the component (A) was significantly observed in the skin groove of the skin texture.

TABLE 1

| | Component (mass %) | Example 1 | Example 2 | Example 3 | Example 4 | Example 5 | Example 6 |
|---|---|---|---|---|---|---|---|
| (A) | Octyltriethoxysilane-treated zinc oxide *1 | 5 | 10 | 15 | 20 | — | 25 |
| | Silicone-treated zinc oxide *2 | — | — | — | — | 20 | — |
| | Aluminum stearate-treated titanium oxide *3 | 5 | 5 | 10 | 10 | 10 | 10 |
| | PEG-10 DIMETHICONE *4 | — | — | — | — | — | — |
| (B) | Polyethylene glycol (30) dipolyhydroxystearate *5 | 1.9 | 1.9 | 1.9 | 1.9 | 1.9 | 1.9 |
| | Sorbitan monoisostearate *6 | 0.95 | 0.95 | 0.95 | 0.95 | 0.95 | 0.95 |
| | C30-45 alkyldimethylsilyl polypropylsilsesquioxane *7 | — | — | — | — | — | — |
| | C30-45 alkyl methicone *8 | — | — | — | — | — | — |
| | 1,3-butylene glycol | 8 | 8 | 8 | 8 | 8 | 8 |

TABLE 1-continued

| | Component (mass %) | Example 1 | Example 2 | Example 3 | Example 4 | Example 5 | Example 6 |
|---|---|---|---|---|---|---|---|
| (D) | Purified water | 5 | 5 | 5 | 5 | 5 | 5 |
| (C) | Dimethylpolysiloxane *9 | 6 | 6 | 6 | 6 | 6 | 6 |
| | Light liquid isoparaffin *10 | 12 | 12 | 12 | 12 | 12 | 12 |
| | Cyclopentasiloxane *11 | 56.15 | 51.15 | 41.15 | 36.15 | 36.15 | 31.15 |
| Total | | 100 | 100 | 100 | 100 | 100 | 100 |
| Content of Component (A) (mass %) | | 10 | 15 | 25 | 30 | 30 | 35 |
| Content of Component (C) (mass %) | | 74.15 | 69.15 | 59.15 | 54.15 | 54.15 | 49.15 |
| Mass ratio [(B)/(A)] | | 0.190 | 0.127 | 0.076 | 0.063 | 0.063 | 0.054 |
| SPF | | 5.6 | 7.1 | 30.2 | 33.2 | 33.2 | 40.9 |
| Water resistance (%) | | >100 | >100 | 87 | 89 | 89 | 91 |
| Viscosity (mPa · s) | | 50 | 98 | 384 | 984 | 796 | 1244 |
| Absence of white residue | | A | A | B | B | A | C |
| Easiness to spread | | A | A | A | A | A | A |

TABLE 2

| | Component (mass %) | Example 7 | Example 8 | Example 9 | Example 10 |
|---|---|---|---|---|---|
| (A) | Octyltriethoxysilane-treated zinc oxide *1 | 20 | 20 | 20 | 20 |
| | Silicone-treated zinc oxide *2 | — | — | — | — |
| | Aluminum stearate-treated titanium oxide *3 | 10 | 10 | 10 | 10 |
| | PEG-10 DIMETHICONE *4 | — | — | — | — |
| (B) | Polyethylene glycol (30) dipolyhydroxystearate *5 | 1.9 | 1.9 | 1.9 | 1.9 |
| | Sorbitan monoisostearate *6 | 0.95 | 0.95 | 0.95 | 0.95 |
| (E) | C30-45 alkyldimethylsilyl polypropylsilsesquioxane *7 | 0.6 | 1.2 | 3 | — |
| | C30-45 alkyl methicone *8 | — | — | — | 1.2 (0.66) |
| | 1,3-butylene glycol | 8 | 8 | 8 | 8 |
| (D) | Purified water | 5 | 5 | 5 | 5 |
| (C) | Dimethylpolysiloxane *9 | 6 | 6 | 6 | 6 |
| | Light liquid isoparaffin *10 | 12 | 12 | 12 | 12 |
| | Cyclopentasiloxane *11 | 35.55 | 34.95 | 33.15 | 34.95 |
| Total | | 100 | 100 | 100 | 100 |
| Content of Component (A) (mass %) | | 30 | 30 | 30 | 30 |
| Content of Component (C) (mass %) | | 53.55 | 52.95 | 51.15 | 52.95 |
| Mass ratio [(B)/(A)] | | 0.063 | 0.063 | 0.063 | 0.063 |
| SPF | | 45.9 | 49.2 | 51.2 | 44.8 |
| Water resistance (%) | | 93 | 96 | 99 | 94 |
| Viscosity (mPa · s) | | 1354 | 1899 | 10480 | 2370 |
| Absence of white residue | | B | B | C | B |
| Easiness to spread | | A | A | C | A |

The numerical value in the parenthesis in the table means the content of the active component relative to the cosmetic.

TABLE 3

| | Component (mass %) | Comparative Example 1 | Example 11 | Example 12 | Example 8 | Example 13 | Comparative Example 2 |
|---|---|---|---|---|---|---|---|
| (A) | Octyltriethoxysilane-treated zinc oxide *1 | 20 | 20 | 20 | 20 | 20 | 20 |
| | Silicone-treated zinc oxide *2 | — | — | — | — | — | — |
| | Aluminum stearate-treated titanium oxide *3 | 10 | 10 | 10 | 10 | 10 | 10 |
| | PEG-10 DIMETHICONE *4 | — | — | — | — | — | — |
| (B) | Polyethylene glycol (30) dipolyhydroxystearate *5 | 0.15 | 0.4 | 1.9 | 1.9 | 3.8 | 6.5 |
| | Sorbitan monoisostearate *6 | — | — | — | 0.95 | 0.95 | 0.95 |
| | C30-45 alkyldimethylsilyl polypropylsilsesquioxane *7 | — | — | — | 1.2 | 1.2 | 1.2 |
| | C30-45 alkyl methicone *8 | — | — | — | — | — | — |
| | 1,3-butylene glycol | 8 | 8 | 8 | 8 | 8 | 8 |

TABLE 3-continued

| | Component (mass %) | Comparative Example 1 | Example 11 | Example 12 | Example 8 | Example 13 | Comparative Example 2 |
|---|---|---|---|---|---|---|---|
| (D) | Purified water | 5 | 5 | 5 | 5 | 5 | 5 |
| (C) | Dimethylpolysiloxane *9 | 6 | 6 | 6 | 6 | 6 | 6 |
| | Light liquid isoparaffin *10 | 12 | 12 | 12 | 12 | 12 | 12 |
| | Cyclopentasiloxane *11 | 38.85 | 38.60 | 37.10 | 34.95 | 33.05 | 30.35 |
| Total | | 100 | 100 | 100 | 100 | 100 | 100 |
| Content of Component (A) (mass %) | | 30 | 30 | 30 | 30 | 30 | 30 |
| Content of Component (C) (mass %) | | 56.85 | 56.60 | 55.10 | 52.95 | 51.05 | 48.35 |
| Mass ratio [(B)/(A)] | | 0.005 | 0.013 | 0.063 | 0.063 | 0.127 | 0.217 |
| SPF | | 47.4 | 45.1 | 42.4 | 49.2 | 60.2 | 55.2 |
| Water resistance (%) | | 50 | 70 | 75 | 96 | 75 | 61 |
| Viscosity (mPa · s) | | 1536 | 1442 | 1267 | 1899 | 2185 | 2517 |
| Absence of white residue | | B | B | B | B | B | B |
| Easiness to spread | | A | A | A | A | A | A |

TABLE 4

| | Component (mass %) | Example 4 | Comparative Example 3 | Comparative Example 4 | Example 4 | Comparative Example 5 |
|---|---|---|---|---|---|---|
| (A) | Octyltriethoxysilane-treated zinc oxide *1 | 20 | 20 | 20 | 20 | 20 |
| | Silicone-treated zinc oxide *2 | — | — | — | — | — |
| | Aluminum stearate-treated titanium oxide *3 | 10 | 10 | 10 | 10 | 10 |
| | PEG-10 DIMETHICONE *4 | — | 1.9 | — | — | — |
| (B) | Polyethylene glycol (30) dipolyhydroxystearate *5 | 1.9 | — | — | 1.9 | 1.9 |
| | Sorbitan monoisostearate *6 | 0.95 | — | 0.95 | 0.95 | 0.95 |
| | C30-45 alkyldimethylsilyl polypropylsilsesquioxane *7 | — | — | — | — | — |
| | C30-45 alkyl methicone *8 | — | — | — | — | — |
| | 1,3-butylene glycol | 8 | 8 | 8 | 8 | 8 |
| (D) | Purified water | 5 | 5 | 5 | 5 | 25 |
| (C) | Dimethylpolysiloxane *9 | 6 | 6 | 6 | 6 | 6 |
| | Light liquid isoparaffin *10 | 12 | 12 | 12 | 12 | 12 |
| | Cyclopentasiloxane *11 | 36.15 | 37.10 | 38.05 | 36.15 | 16.15 |
| Total | | 100 | 100 | 100 | 100 | 100 |
| Content of Component (A) (mass %) | | 30 | 30 | 30 | 30 | 30 |
| Content of Component (C) (mass %) | | 54.15 | 55.10 | 56.05 | 54.15 | 34.15 |
| Mass ratio [(B)/(A)] | | 0.063 | 0.000 | 0.000 | 0.063 | 0.063 |
| SPF | | 33.2 | 33.9 | 41.6 | 33.2 | 20.2 |
| Water resistance (%) | | 89 | 68 | 58 | 89 | 32 |
| Viscosity (mPa · s) | | 984 | 7560 | 1952 | 984 | >100,000 |
| Absence of white residue | | B | C | B | B | C |
| Easiness to spread | | A | C | B | A | D |

The symbols in the tables indicate the followings:

1: MZX-3040TS (average particle diameter: 0.035 μm, manufactured by Tayca Corporation);

2: MZ-504R3M (average particle diameter: 0.025 μm, manufactured by Tayca Corporation);

3: MT-100TV (average particle diameter: 0.015 μm, manufactured by Tayca Corporation);

4: KF-6017 (manufactured by Shin-Etsu Chemical Co., Ltd.);

5: Cithrol DPHS-SO-(AP) (manufactured by Croda Japan K.K.);

6: SPAN (R) 120-LQ-(RB) (manufactured by Croda Japan K.K.);

7: SW-8005 C30 Resin Wax (melting point: 63° C. to 71° C., manufactured by DuPont Toray Specialty Materials K.K.);

8: AMS-C30 Cosmetic Wax (melting point: 73° C. to 77° C., manufactured by DuPont Toray Specialty Materials K.K.), active component content: 55 mass %;

9: KF-96A-10CS (manufactured by Shin-Etsu Chemical Co., Ltd.);

10: PARLEAM 4 (manufactured by NOF Corporation); and

11: TSF405A (manufactured by Momentive Performance Materials Japan LLC).

The invention claimed is:

1. A water-in-oil emulsified sunscreen cosmetic, comprising the following components:

(A) 10 mass % or more and 50 mass % or less of a hydrophobized ultraviolet scattering agent;

(B) a dipolyhydroxystearic acid ester of a polyhydric alcohol;

(C) 35 mass % or more and 85 mass % or less of a liquid oil agent; and (D) water;

wherein a mass ratio of the component (B) to the component (A), [(B)/(A)], is 0.01 or more and 0.2 or less, wherein a content of an ultraviolet absorbing agent is 0 mass % or more and 5 mass % or less, and said cosmetic further comprises 0.4 mass % to 2 mass % of (E) an alkyl modified silicone wax having a melting point of 60° C. or more.

2. The water-in-oil emulsified sunscreen cosmetic according to claim 1, wherein the component (A) is a hydrophobized fine particle metal oxide.

3. The water-in-oil emulsified sunscreen cosmetic according to claim 1, wherein the component (A) is one or more fine particle metal oxides selected from the group consisting of zinc oxide, titanium oxide, and cerium oxide, and wherein the component (A) is subjected to hydrophobization treatment.

4. The water-in-oil emulsified sunscreen cosmetic according to claim 1, wherein the component (B) is polyalkylene glycol dipolyhydroxystearate.

5. The water-in-oil emulsified sunscreen cosmetic according to claim 1, wherein a content of the component (B) in the water-in-oil emulsified sunscreen cosmetic is 0.5 mass % or more and 5 mass % or less.

6. The water-in-oil emulsified sunscreen cosmetic according to claim 1, wherein a content of the component (C) in the water-in-oil emulsified sunscreen cosmetic is 45 mass % or more and 70 mass % or less.

7. The water-in-oil emulsified sunscreen cosmetic according to claim 1, wherein a content of the component (C) in the water-in-oil emulsified sunscreen cosmetic is 47.5 mass % or more and 65 mass % or less.

8. The water-in-oil emulsified sunscreen cosmetic according to claim 1, wherein a content of the component (C) in the water-in-oil emulsified sunscreen cosmetic is 50 mass % or more and 60 mass % or less.

9. The water-in-oil emulsified sunscreen cosmetic according to claim 1, wherein a mass ratio of the component (A) to the component (C), [(A)/(C)], is 0.03 or more and 2 or less.

10. The water-in-oil emulsified sunscreen cosmetic according to claim 1, wherein a mass ratio of the component (B) to the component (C), [(B)/(C)], is 0.001 or more and 0.15 or less.

11. The water-in-oil emulsified sunscreen cosmetic according to claim 1, wherein a content of the component (D) in the water-in-oil emulsified sunscreen cosmetic is 0.1 mass % or more and 25 mass % or less.

12. The water-in-oil emulsified sunscreen cosmetic according to claim 1, wherein a mass ratio of the component (D) to the component (C), [(D)/(C)], is 0.005 or more and 1 or less.

13. The water-in-oil emulsified sunscreen cosmetic according to claim 1, wherein a content of an ultraviolet absorbing agent is 0 mass %.

14. A water-in-oil emulsified sunscreen cosmetic, comprising the following components:

(A) 10 mass % or more and 50 mass % or less of a hydrophobized ultraviolet scattering agent;

(B) a dipolyhydroxystearic acid ester of a polyhydric alcohol;

(C) 35 mass % or more and 85 mass % or less of a liquid oil agent; and (D) water;

wherein a mass ratio of the component (B) to the component (A), [(B)/(A)], is 0.01 or more and 0.2 or less, wherein a content of an ultraviolet absorbing agent is 0 mass % or more and 5 mass % or less, said cosmetic further comprises 0.4 mass % to 2 mass % of (E) an alkyl modified silicone wax having a melting point of 60° C. or more, and said component (E) is one or more selected from the group consisting of an alkyl methicone wax having a melting point of 60° C. or more, an alkyl dimethicone wax having a melting point of 60° C. or more, and a silsesquioxane resin wax having a melting point of 60° C. or more.

15. The water-in-oil emulsified sunscreen cosmetic according to claim 14, wherein the component (A) is a hydrophobized fine particle metal oxide.

16. The water-in-oil emulsified sunscreen cosmetic according to claim 14, wherein the component (A) is one or more fine particle metal oxides selected from the group consisting of zinc oxide, titanium oxide, and cerium oxide, and wherein the component (A) is subjected to hydrophobization treatment.

17. The water-in-oil emulsified sunscreen cosmetic according to claim 14, wherein the component (B) is polyalkylene glycol dipolyhydroxystearate.

18. The water-in-oil emulsified sunscreen cosmetic according to claim 14, wherein a content of the component (B) in the water-in-oil emulsified sunscreen cosmetic is 0.5 mass % or more and 5 mass % or less.

19. The water-in-oil emulsified sunscreen cosmetic according to claim 14, wherein a content of the component (C) in the water-in-oil emulsified sunscreen cosmetic is 45 mass % or more and 70 mass % or less.

20. The water-in-oil emulsified sunscreen cosmetic according to claim 14, wherein a content of the component (C) in the water-in-oil emulsified sunscreen cosmetic is 47.5 mass % or more and 65 mass % or less.

* * * * *